United States Patent
Esposito

(10) Patent No.: US 6,511,320 B2
(45) Date of Patent: Jan. 28, 2003

(54) DENTAL INSTRUMENTS AND METHOD FOR INCREASING PATIENT COMFORT

(75) Inventor: Robert L. Esposito, 2515 Main St., Lafayette, IN (US) 47904-3337

(73) Assignee: Robert L. Esposito, Lafayette, IN (US)

( * ) Notice: Subject to any disclaimer, the term of this patent is extended or adjusted under 35 U.S.C. 154(b) by 0 days.

(21) Appl. No.: 09/781,359

(22) Filed: Feb. 12, 2001

(65) Prior Publication Data

US 2002/0110782 A1 Aug. 15, 2002

(51) Int. Cl.[7] .................................................. A61C 3/00
(52) U.S. Cl. ........................................................ 433/141
(58) Field of Search ................................ 433/141, 146, 433/147, 142, 143, 72, 75

(56) References Cited

U.S. PATENT DOCUMENTS

| | | | |
|---|---|---|---|
| 797,270 A | 8/1905 | Dreher | |
| 1,202,698 A | 10/1916 | Ford | |
| 3,562,913 A | * 2/1971 | Saffro | 433/75 |
| 3,852,884 A | 12/1974 | Lazarus | |
| D249,062 S | 8/1978 | Crafoord et al. | D24/10 |
| 4,323,347 A | 4/1982 | Weissman | 433/141 |
| 4,836,781 A | 6/1989 | Meinershagen | 433/141 |
| 5,090,907 A | 2/1992 | Hewitt et al. | 433/144 |
| 5,127,833 A | * 7/1992 | Kline | 433/143 |
| 5,161,971 A | 11/1992 | Neiner et al. | 433/141 |
| 5,407,358 A | 4/1995 | Gruber | 433/141 |
| 5,501,597 A | 3/1996 | Wilson | 433/141 |

* cited by examiner

Primary Examiner—John J. Wilson
Assistant Examiner—Melba Bumgarner
(74) Attorney, Agent, or Firm—Guy Cumberbatch

(57) ABSTRACT

A dental instrument (10) has an elongated shaft (16) and a user grip handle (26). A dental tool (12) extends from one end (18) of the shaft (16). A rotatable sleeve (14) is rotatably mounted to the shaft (16) and rotates relative to the shaft (16) and the dental tool (12). The rotatable sleeve (14) is mounted to the shaft (16) between the user grip handle (26) and the dental tool (12). During use of the dental instrument (10) the rotatable sleeve (14) contacts a portion of the patient's mouth and rotates as the dental instrument (10) is moved to provide greater comfort to the patient.

22 Claims, 1 Drawing Sheet

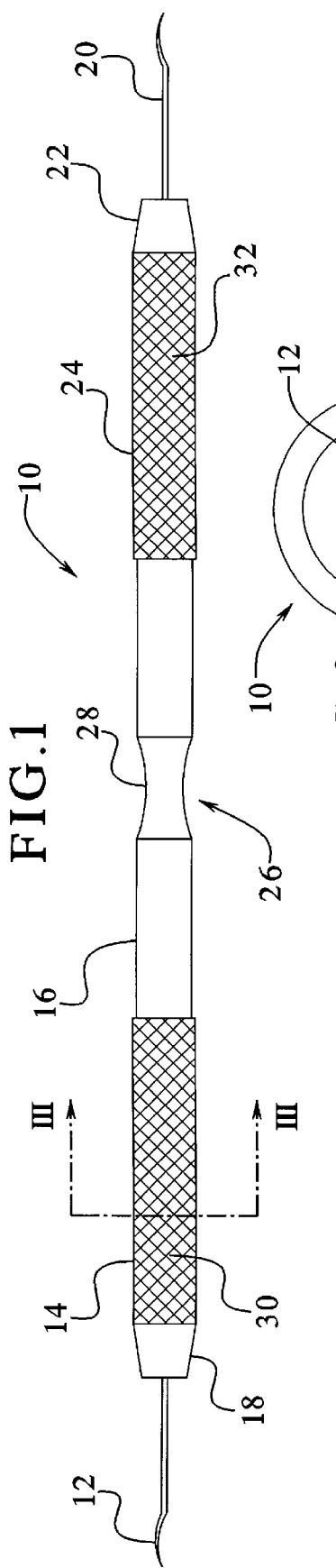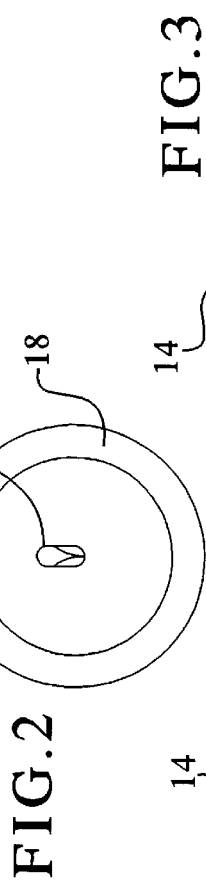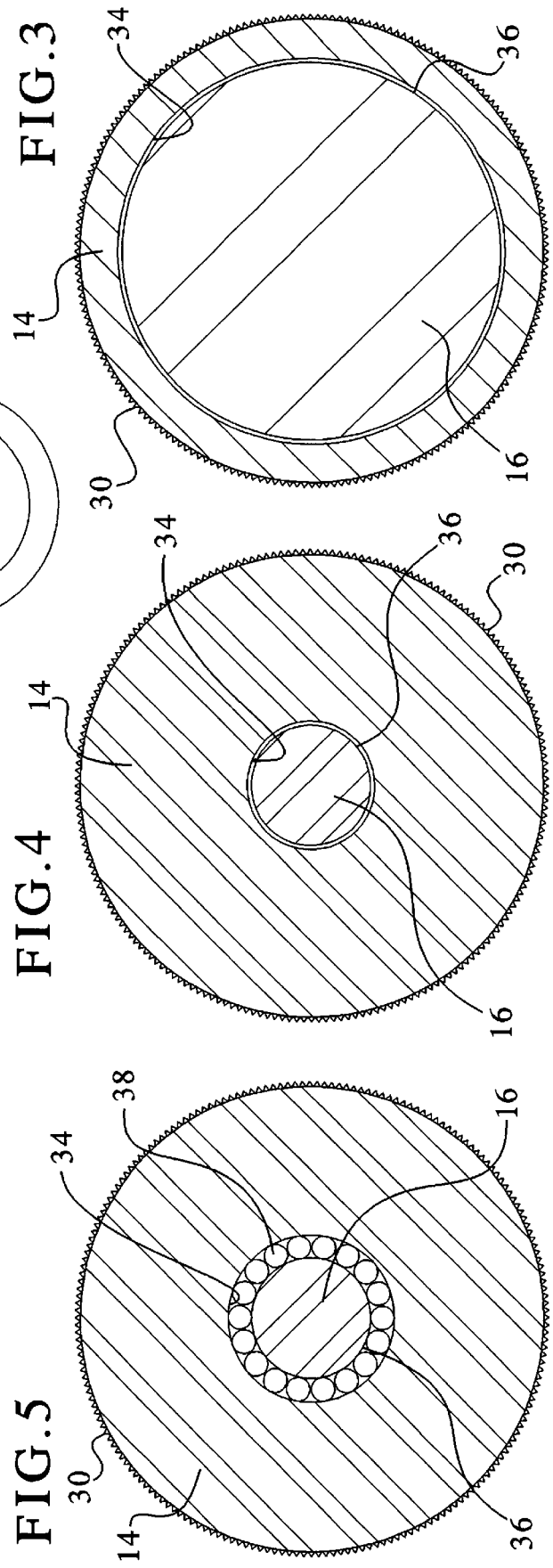

DENTAL INSTRUMENTS AND METHOD FOR INCREASING PATIENT COMFORT

FIELD OF THE INVENTION

The present invention generally relates to dental instruments. More specifically, the present invention relates to dental instruments which have a rotatable portion that can rotate when in contact with and moved along a patient's mouth. The rotatable portion provides enhanced comfort to the patient during a dental procedure. The present invention also relates to methods of making the dental instruments and methods of using the dental instruments.

BACKGROUND OF THE INVENTION

A wide variety of dental instruments are in use today and have been used in the past. Dental instruments are typically held in a dental professional's hand with a dental tool at an end of the instrument positioned within a patient's mouth for performing a procedure. Numerous types of dental tools exist for performing many different dental procedures. Some dental tools are fixed in position relative to the rest of dental instrument, while other dental tools may be movable relative to the rest of the dental instrument. For example, some dental tools may be manually rotated or may be power driven to rotate.

During a dental procedure it is common for part of the dental instrument other than the dental tool to contact various portions of the patient's mouth. Such contact with the patient may occur at the patient's lower lip, upper lip, teeth, gums, tongue, or other portions of the mouth. The contact of the dental instrument with the patient's mouth may be incidental to the actual procedure within the mouth, or even desired, for example, by supporting the dental instrument on the patient's lip. The contact of the dental instrument with the patient can be a source discomfort for the patient. For example, a dental instrument may be dragged across a patient's lip and scrape the lip which provides discomfort to the patient. The patient's discomfort may be increased when the dental instrument surface scraping the lip has a cross-hatched surface which is commonly used on dental instruments.

Many people are already hesitant to submit themselves to dental procedures. Furthermore, many dental patients experience discomfort during dental procedures. Accordingly, needs exist to improve dental procedures. Needs further exist to enhance patient comfort by reducing discomfort during dental procedures.

Examples of existing dental instruments can be found in U.S. Pat. No. DES 249,062, titled Dental Instrument, which issued on Aug. 22, 1978; U.S. Pat. No. 797,270, titled Tool For Dental Operation, which issued on Aug. 15, 1905; U.S. Pat. No. 3,852,884, titled Winding and Tightening Tool and Method for Manufacturing Same, which issued on Dec. 10, 1974; U.S. Pat. No. 4,323,347, titled Dental Tool for Use with Dental Retaining Splints, which issued on Apr. 6, 1982; U.S. Pat. No. 4,836,781, titled Dental Tool with Dual Restoration Material Retainers, which issued on Jun. 6, 1989; U.S. Pat. No. 5,090,907, titled Dental Curette With Finger Pad, which issued on Feb. 25, 1992; U.S. Pat. No. 5,161,971, titled Dental Instrument, which issued on Nov. 10, 1992; and U.S. Pat. No. 5,501,597, titled Dental Instrument with Gripping Handle and Method for Manufacturing the Same, which issued on Mar. 26, 1996.

SUMMARY OF THE INVENTION

The present invention provides new dental instruments which have a movable surface that contacts the patient. The movable surface provides enhanced comfort to the patient during the dental procedure. The movable surface in contact with the patient allows the dental instrument to be moved and positioned as needed during the dental procedure while reducing unnecessary abrasive contact with the patient. For example, the movable surface can be a rotatable sleeve which rolls along a patient's lip to reduce or eliminate dragging and scraping contact of the dental instrument with the patient's lip. Accordingly, the new dental instruments can enhance patient treatment and improve the quality of dental care.

According to one aspect of the present invention, a dental instrument is provided which has an elongated shaft that has a user grip portion. A dental tool extends from one end of the shaft. A sleeve is provided between the user grip portion and the dental tool. The sleeve is rotatably mounted to the shaft and rotatable relative to the shaft and the dental tool. The sleeve may have an exterior grip enhanced surface. The dental tool may be secured to the end of the shaft in a fixed position or may be movable, such as rotatable. The sleeve can be mounted to the shaft in any way to allow the rotation. Another aspect of the dental instrument is that the sleeve is rotatable in both clockwise and counterclockwise directions. Another dental tool may extend from another end of the shaft and another rotatable sleeve may be rotatably mounted to the shaft. The second sleeve is positioned between the second dental tool and the user grip portion and is rotatable relative to the shaft in the second dental tool.

According to another aspect of the present invention, a dental instrument is provided which has a main body having a user grip portion between first and second end portions. A first tool is mounted to the first end portion, and a first rotatable surface is positioned between the first tool and the user grip portion. A second tool is mounted to the second end portion, and a second rotatable surface is positioned between the second tool and the user grip portion.

According to another aspect of the present invention, a dental instrument for use on a patient is provided which has a dental tool mounted to user handle. The dental instrument has a means for free movement in alternative directions relative to the dental tool while being in contact with a patient during use. A sleeve rotatably mounted to the user handle may be provided for the free movement means.

According to another aspect of the present invention, a method of using a dental instrument on a patient provides positioning a dental tool portion of the dental instrument inside of the patient's mouth, contacting a lip contact portion of the dental instrument to the patient's lip, and moving the dental instrument while rolling the lip contact portion on the patient's lip. The method of using the dental instrument may also include removing the dental tool portion from the patient's mouth and the lip contact portion from the patient's lip, positioning a second dental tool portion of the dental instrument inside of the patient's mouth, contacting a second lip portion of the dental instrument to the patient's lip, and moving the dental instrument while rolling the lip contact portion on the patient's lip. The method of using the dental instrument may also include selectively preventing rolling of the lip contact portion.

Various advantages, feature, and objects of the present invention can become apparent upon reading this disclosure including the appended claims with reference to the accompanying drawings. The advantages, objects, and features may be desired, but not necessarily required to practice the present invention.

BRIEF DESCRIPTION OF THE DRAWINGS

FIG. 1 is an elevational view of a dental instrument according to the principles of the present invention.

FIG. 2 is a left side view of the dental instrument of FIG. 1.

FIG. 3 is a cross-sectional view of the dental instrument of FIG. 1 along the line III—III.

FIG. 4 is a cross-sectional view similar to FIG. 3 and showing an alternative embodiment of the dental instrument according to the present invention.

FIG. 5 is a cross-sectional view similar to FIG. 3 and showing another alternative embodiment of the dental instrument according to the present invention.

DETAILED DESCRIPTION OF THE PREFERRED EMBODIMENTS

Although the present invention can be made in many different forms, the presently preferred embodiments are described in this disclosure and shown in the attached drawings This disclosure exemplifies the principles of the present invention and does not limit the broad aspects of the invention only to the illustrated embodiments.

A new dental instrument 10 according to the principles of the present invention is shown by way of example in FIGS. 1 and 2. Generally, the dental instrument 10 has a rotatable surface between an instrument end and a middle section of the instrument 10. The rotatable surface rotates when it contacts the patient in a rolling manner when the instrument moves along the patient's mouth. The rotatable surface provides comfort to the patient because of the rolling contact rather than a sliding, scraping, or heavy friction contact with the patient's mouth.

Referring to FIGS. 1–3, the dental instrument 10 has a dental tool 12, a rotatable sleeve or surface 14, and an elongated shaft or main body 16. The dental tool 12 extends from an end portion 18 of the shaft 16. The rotatable sleeve 14 is rotatably mounted on the shaft 16. The dental instrument 10 may optionally be a dual tool instrument. The dual tool dental instrument 10 shown in FIG. 1 has another dental tool 20 extending from an opposite end portion 22 of the shaft 16. A second rotatable sleeve or surface 24 is rotatably mounted to the shaft 16.

The dental tools 12, 20 can be any desired tools. Different dental tools may be utilized for different procedures. For example, the dental tool 12 may be used for scraping the patient's teeth to remove plaque and the dental tool 20, at the other end of the dental instrument 10, could be used to probe the patient's gums. The dental tools 12, 20 are shown as being secured to their respective end portions 18, 22 of the shaft 16 in fixed positions, i.e. not movable relative to the shaft 16. However, the dental tools 12, 20 can be mounted in any desired manner, such as removable or movable. Also, the dental tool 12 could be rotationally mounted and driven by a power source. In such a device, most likely the other end of the dental instrument 10 would not include the second dental tool 20, but rather would have a power feed. Examples of power sources for the dental tool 12 include, for example, pneumatic power, electric power, and other power sources.

The dental instrument 10 has a user grip portion or user handle 26 shown generally in the middle of dental instrument 10. The user grip portion 26 is the portion of the shaft 16 shown between the two rotatable sleeves 14, 24. If the dental instrument 10 is a single tooled device, i.e. only having one dental tool 12 without the second dental tool 20, then the user grip portion 26 may actually form an end of the dental instrument 10. A person using the dental instrument 10 may grip and hold the dental instrument 10 by the user grip portion 26. Holding the dental instrument 10 by the user grip portion 26 allows the rotatable sleeve 14 to rotate about the longitudinal axis of the dental instrument 10 during use. Grip enhanced mechanisms can be provided on the user grip portion 26, if desired. For example a recess 28 can be provided to enhance secure holding of the dental instrument 10.

The user grip portion 26 in the example of the present invention is rigidly connected the end portions 18, 22, as all being part of the shaft 16. However, any other suitable shapes and structures, movable or not, are contemplated by the invention.

The rotatable sleeves 14, 24 are rotatably mounted on the shaft 16. The rotatable sleeves 14, 24 freely rotate in an unrestricted manner in both clockwise and, alternatively, counterclockwise directions. During use of the dental instrument 10, the dental tool 12 is placed inside of a patient's mouth. The rotatable sleeve 14 may contact a portion of the patient's mouth, for example the patient's lips, teeth, gums, or other area of the patient. As the dental instrument 10 is moved relative to the patient's mouth, the rotatable sleeve 14 rolls along the points of contact with the patient while rotating about its longitudinal axis. In this manner, the dental instrument 10 does not slide along the patient contact points which tend to cause discomfort to the patient. Accordingly, the rotatable sleeve 14 enhances patient comfort by providing a gentler contact with the patient. If desired, the operator of the dental instrument 10 can grip the shaft 16 and the rotatable sleeve 14 at the same time and prevent rotation of the rotatable sleeve 14. The sleeve 14 can be movable, for example, slidable longitudinally along the shaft 16, or fixed in position in the longitudinal direction. The other sleeve 24 at the opposite end of the dental instrument 10 operates similarly.

The rotatable sleeve 14 rotates relative to the shaft 16 and the dental tool 12. In other words, the rotatable sleeve 14 rotates independently of the shaft 16 and the dental tool 12. The rotatable sleeve 14 is shown as being mounted on the shaft 16 between the user grip portion 26 and the dental tool 12. Similarly, the second rotatable sleeve 24 is shown as being mounted on the shaft 16 between the dental tool 20 and the user grip portion 26.

The rotatable sleeves 14, 24 may have an outer exterior grip enhanced surface 30, 32 respectively. For example the grip enhanced surfaces 30, 32 may be cross-hatched surfaces. The grip enhanced surfaces 30, 32 allow the operator of the dental instrument to have a greater secured grip of the dental instrument 10 when gripping the rotatable sleeves 14, 24.

The rotatable sleeves 14, 24 are shown as having a generally cylindrical shape, but may have other shapes as desired. Also, the shaft 16 is shown as having a generally cylindrical shape, but it can have any shape as desired in cross-section or otherwise. The rotatable sleeves 14, 24 are located adjacent their respective dental tools 12, 20 so that when the dental tool 12 or the dental tool 20 is positioned within the patient's mouth the respective rotatable sleeves 14, 24 can contact the patient's mouth. The rotatable sleeves 14, 24 being adjacent their respective dental tools 12, 20 means that they can be immediately next to the dental tools 12, 20 or spaced away from the dental tools 12, 20 as long as the rotatable sleeves 14, 24 are in a position to contact the patient and rotate during use of the dental instrument 10.

FIG. 3 shows a cross section of the dental instrument 10 along the line III—III of FIG. 1. The rotatable sleeve 14 is rotatably mounted to the shaft 16 simply by having a slightly larger inside diameter than the outside diameter of the shaft 16. The inner diameter surface 34 of the rotatable sleeve 14 slides rotatably relative to the outer diameter surface 36 of the shaft 16. Friction between the inner diameter surface 34 and the outer diameter surface 36 can be reduced, for example by polishing the surfaces or providing a lubricant. The rotatable sleeve 14 shown in FIG. 3 has a relatively thin thickness in cross-section compared to the diameter of the shaft 16.

FIG. 4 shows an alternative embodiment of the dental instrument 10 in which like components are labeled with the same reference numerals. The rotatable sleeve 14 of FIG. 4 has a greater wall thickness in cross section compared to the rotatable sleeve 14 of FIG. 3. Similarly, the diameter of the shaft 16 of FIG. 4 is less than the diameter of the shaft 16 shown in FIG. 3. Referring to FIG. 4, the wall thickness of the rotatable sleeve 14 is greater than the diameter of the shaft 16 where the sleeve 14 is mounted to the shaft 16.

FIG. 5 shows another alternative embodiment of the dental instrument 10 with like reference numerals referring to like components. The rotatable sleeve 14 is rotatably mounted to the shaft 16 by a bearing 38, such as one that has rolling elements as shown between the sleeve and shaft. Accordingly, the present invention contemplates any structure for allowing the sleeve 14 to rotate.

All of the components of the dental instrument 10 can be made out of material suitable for dental use, for example, stainless steel. Also, the rotatable sleeves 14, 24 could be made from materials which are softer and more resilient than metal materials. For example, plastics, rubbers, polyurethanes, or composite materials could used for the rotatable sleeves 14, 24. If such materials are used it may be appropriate to remove the sleeves 14, 24 after use on a patient and dispose of the used sleeves. New, clean sleeves would then be placed on the dental instrument 10 after the instrument is appropriately cleaned for the next use. The dental instrument can be cleaned according to standard dental practices, for example by autoclaving and cleaning baths.

While the presently preferred embodiments have been illustrated and described, numerous changes and modifications can be made without significantly departing from the spirit and scope of this invention. Therefore, the inventor intends that such changes and modifications are covered by the appended claims.

The invention is claim as:

1. A dental instrument for use in a patient's mouth, comprising:
   an elongated shaft having a user grip portion;
   an end portion fixed axially on one end of the shaft;
   a dental tool extending from the end portion away from the shaft; and
   a patient contact sleeve between the user grip portion and the end portion rotatably mounted to the shaft and rotatable relative to the shaft and the dental tool, the end portion axially constraining the patient contact sleeve on the shaft, the patient contact sleeve so constructed and arranged and having a length such that when the dental instrument is in use in the patient's mouth, the patient contact sleeve contacts the patient's mouth and rotates when the dental instrument is moved along the patient's mouth.

2. The dental instrument of claim 1, wherein the sleeve has an exterior grip enhanced surface.

3. The dental instrument of claim 1, wherein the dental tool is secured to the end of the shaft in a fixed position.

4. The dental instrument of claim 1, wherein the patient contact sleeve has an inner diameter surface in rotatable contact with an outer diameter surface of the shaft.

5. The dental instrument of claim 1, wherein the patient contact sleeve is rotatably mounted to the shaft by a bearing.

6. The dental instrument of claim 1, wherein the patient contact sleeve has a generally cylindrical shape.

7. The dental instrument of claim 6, wherein a wall thickness of the generally cylindrical shaped patient contact sleeve is less than a diameter of the shaft at a portion of the shaft where the sleeve is mounted.

8. The dental instrument of claim 6, wherein a wall thickness of the generally cylindrical shaped patient contact sleeve is greater than a diameter of the shaft at a portion of the shaft where the sleeve is mounted.

9. The dental instrument of claim 1, wherein the patient contact sleeve is made of metal.

10. A dental instrument for use in a patient's mouth, comprising:
    a main body having a user grip portion between first and second end portions;
    a first tool mounted to the first end portion;
    a first rotatable patient contact surface positioned between the first tool and the user grip portion, the first end portion axially constraining the first patient contact surface on the main body, the first rotatable patient contact surface so constructed and arranged and having a length such that when the dental instrument is in use in the patient's mouth the first rotatable patient contact surface contacts the patient's mouth and rotates when the dental instrument is moved along the patient's mouth;
    a second tool mounted to the second end portion; and
    a second rotatable patient contact surface positioned between the second tool and the user grip portion, the second end portion axially constraining the second patient contact surface on the main body, the second rotatable patient contact surface so constructed and arranged and having a length such that when the dental instrument is in use in the patient's mouth the second rotatable patient contact surface contacts the patient's mouth and rotates when the dental instrument is moved along the patient's mouth.

11. The dental instrument of claim 10, wherein at least one of the first and second rotatable patient contact surfaces has an exterior grip enhanced surface.

12. The dental instrument of claim 10, wherein at least one of the first and second tools are mounted in a fixed position relative to the main body.

13. The dental instrument of claim 10, wherein at least one of the first and second rotatable patient contact surfaces are rotatably mounted by a bearing.

14. The dental instrument of claim 10, wherein at least one of the first and second rotatable patient contact surfaces is made of metal.

15. The dental instrument of claim 10, wherein each of the first and second rotatable contact surfaces has a lip contact portion having a length such that when each of the first and second tools, respectively, is inside the patient's mouth during use the lip contact portion contacts a lip of the patient and rotates as the lip contact portion moves along the patient's lip.

16. A method of using a dental instrument on a patient having a mouth and a lip, comprising the steps of:
    positioning a dental tool portion of the dental instrument inside of the patient's mouth;
    contacting a lip contact portion of the dental instrument to the patient's lip; and
    moving the dental instrument while rolling the lip contact portion on the patient's lip.

17. The method of using a dental instrument of claim 16, further comprising the steps of:

removing dental tool portion from the patient's mouth and the lip contact portion from the patient's lip;

positioning a second dental tool portion of the dental instrument inside of the patient's mouth;

contacting a second lip contact portion of the dental instrument to the patient's lip; and moving the dental instrument while rolling the second lip contact portion on the patient's lip.

18. The method of using a dental instrument of claim 16, further comprising the step of selectively preventing rolling of the lip contact portion.

19. A dental instrument for use in a patient's mouth, comprising:

an elongated shaft having a user grip portion;

a dental tool extending from one end of the shaft;

a bearing on the shaft wherein the bearing includes rolling elements; and a patient contact sleeve between the user grip portion and the dental tool rotatably mounted via the bearing to the shaft and rotatable relative to the shaft and the dental tool, the patient contact sleeve so constructed and arranged and having a length such that when the dental instrument is in use in the patient's mouth, the patient contact sleeve contacts the patient's mouth and rotates when the dental instrument is moved along the patient's mouth.

20. The dental instrument of claim 19, wherein the patient contact sleeve is made of metal.

21. The dental instrument of claim 19, wherein the dental tool is secured to the end of the shaft in a fixed position.

22. The dental instrument of claim 19, wherein the rolling elements are balls.

* * * * *